(12) United States Patent
Emig et al.

(10) Patent No.: US 6,706,722 B2
(45) Date of Patent: Mar. 16, 2004

(54) HETEROARYL DERIVATIVES AND THEIR USE AS MEDICAMENTS

(75) Inventors: Peter Emig, Bruchköbel (DE); Eckhard Günther, Maintal (DE); Bernd Nickel, Mühltal (DE); Gerhard Bacher, Germering (DE); Silke Baasner, Schöneck (DE); Thomas Beckers, Frankfurt (DE); Beate Aue, Grossostheim (DE)

(73) Assignee: Zentaris AG, Frankfurt (DE)

( * ) Notice: Subject to any disclaimer, the term of this patent is extended or adjusted under 35 U.S.C. 154(b) by 0 days.

(21) Appl. No.: 09/910,142

(22) Filed: Jul. 20, 2001

(65) Prior Publication Data

US 2002/0132821 A1 Sep. 19, 2002

(30) Foreign Application Priority Data

Jul. 21, 2000 (DE) .......................................... 100 35 927

(51) Int. Cl.[7] ................... A61K 31/505; C07D 239/02; C07D 219/00; C07D 243/02
(52) U.S. Cl. ................. 514/269; 514/297; 540/470; 540/553; 540/575; 544/298; 546/102; 546/103; 546/104
(58) Field of Search ................. 514/269, 297; 544/298; 546/102, 103, 104; 540/470, 553, 575

(56) References Cited

U.S. PATENT DOCUMENTS 5,030,631 A * 7/1991 Bauer .......................... 514/218
5,861,395 A 1/1999 Taveras et al. .......... 514/232.8

FOREIGN PATENT DOCUMENTS

| EP | 0 112 776 A2 | 12/1983 |
| EP | 0 831 090 A1 | 9/1997 |
| WO | WO 98/00402 | 1/1998 |
| WO | WO 99/16751 | 4/1999 |
| WO | WO 00/12074 | 3/2000 |
| WO | WO 00/51614 | 9/2000 |

OTHER PUBLICATIONS

Graham J. Atwell, et al., Potential Antitum Agents, J. Med Chem 1987, 30, 664–669.
Arthur G. Taveras, Jeff Deskus, et al., Identification of Pharmacokinetically Stable, 10–Dibromo–8–chlorobenzocycloheptapyridine Farnesyl Protein Transferase Inhibitors with Potent Enzyme and Cellular Activities, J. Med. Chem. 1999, 42, 2651–2661.

* cited by examiner

Primary Examiner—Alan L. Rotman
Assistant Examiner—Tamthom Truong
(74) Attorney, Agent, or Firm—Goodwin Procter LLP

(57) ABSTRACT

The invention relates to novel acridine derivatives of formula 1, to their preparation and to their use as medicaments, in particular for treating tumors.

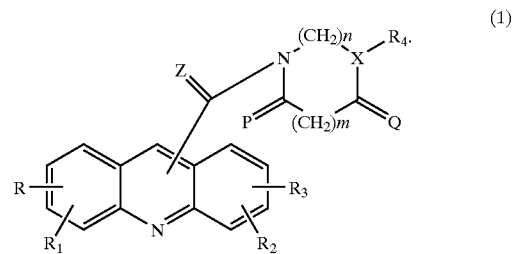

10 Claims, No Drawings

HETEROARYL DERIVATIVES AND THEIR USE AS MEDICAMENTS

BACKGROUND

The invention relates to novel heteroaryl compounds, methods for their preparation, and to a therapeutic process for their use as medicaments, particularly for treating tumors.

DESCRIPTION OF THE INVENTION

According to one aspect of the invention, novel acridine derivatives are provided of the formula (1)

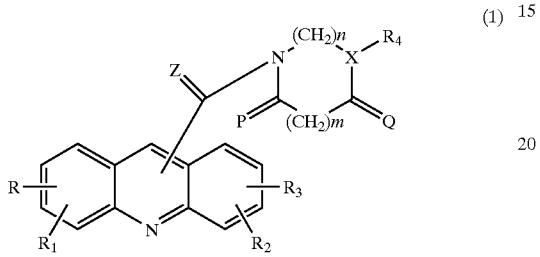

wherein

R, $R_1$, $R_2$, $R_3$ are attached to any of the acridine carbon atoms $C_{1-9}$ and are the same or different and independently of one another are hydrogen, hydroxyl, a straight-chain or branched $C_{1-8}$ alkyl, $C_{3-7}$ cycloalkyl, straight-chain or branched $C_{1-8}$ alkylcarbonyl, suitably acetyl, straight-chain or branched $C_{1-8}$ alkoxy, halogen, aryl-$C_{1-8}$ alkoxy, suitably benzyloxy or phenylethyloxy, nitro, amino, mono-$C_{1-4}$ alkylamino, di-$C_{1-4}$ alkylamino, $C_{1-8}$ alkoxycarbonylamino, $C_{1-6}$ alkoxycarbonylamino-$C_{1-8}$ alkyl, cyano, straight-chain or branched cyano-$C_{1-6}$ alkyl, carboxyl, $C_{1-8}$ alkoxycarbonyl, $C_{1-4}$ alkyl which is substituted by one or more fluorine atoms, suitably the trifluoromethyl group, carboxy-$C_{1-8}$ alkyl or $C_{1-8}$ alkoxycarbonyl-$C_{1-6}$ alkyl, $C_{1-6}$ alkenyl, suitably allyl, $C_{2-6}$ alkynyl, suitably ethynyl or propargyl, straight-chain or branched cyano-$C_{1-6}$ alkyl, suitably cyanomethyl, aryl, where the aryl radical is unsubstituted or mono- or polysubstituted by identical or different substituents from the group of halogen, straight-chain or branched $C_{1-8}$ alkyl, $C_{3-7}$ cycloalkyl, carboxyl, straight-chain or branched $C_{1-8}$ alkoxycarbonyl, suitably tert-butoxycarbonyl, by trifluoromethyl, hydroxyl, straight-chain or branched $C_{1-8}$ alkoxy, suitably methoxy or ethoxy, benzyloxy, nitro, amino, mono-$C_{1-4}$ alkylamino, di-$C_{1-4}$ alkylamino, cyano, straight-chain or branched cyano-$C_{1-6}$ alkyl, Z is oxygen or sulfur, where the radical

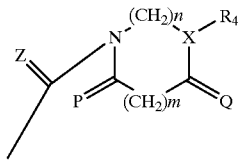

substituted on the acridine heterocycle is attached to a C atom $C_{1-9}$ of the acridine ring skeleton;

P, Q independently of one another represent oxygen or in each case two hydrogen atoms (i.e. —$CH_2$);

X is nitrogen or C—$R_5$, where $R_5$ is hydrogen or $C_{1-6}$ alkyl;

n,m independently of one another denotes a cardinal number between 0 and 3, with the proviso that when n=0, X is a $CR_5R_6$ group where $R_5$ and $R_6$ independently of one another represent hydrogen or $C_{1-6}$ alkyl and that the nitrogen atom adjacent to the C=Z group is substituted by a hydrogen atom or a $C_{1-6}$ alkyl group;

$R_4$ is a straight-chain or branched $C_{1-20}$ alkyl radical which can be saturated or unsaturated, with one to three double and/or triple bonds, and which can be unsubstituted or substituted at the same or different C atoms by one, two or more aryl, heteroaryl, halogen, cyano, —C=NH ($NH_2$), $C_{1-6}$ alkoxycarbonylamino, $C_{1-6}$ alkoxy, amino, mono-$C_{1-4}$ alkylamino or di-$C_{1-4}$ alkylamino; carboxy, $C_{1-4}$ alkoxycarbonyl; a $C_{6-14}$ aryl radical, $C_{6-14}$ aryl-$C_{1-4}$ alkyl radical or a $C_{2-10}$ heteroaryl or $C_{2-10}$ heteroaryl-$C_{1-4}$ alkyl radical which contains one or more heteroatoms that are N, O or S, where the $C_{1-4}$ alkyl radical can be unsubstituted or mono- or polysubstituted with the same or different substituents from the group of $C_{1-6}$ alkyl, halogen or oxo (=O), and where the $C_{6-14}$ aryl or $C_{2-10}$ heteroaryl radical is unsubstituted or mono- or polysubstituted by the same or different substituents from the group of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, straight-chain or branched $C_{1-6}$ alkyl which is substituted by one or more fluorine atoms, suitably trifluoromethyl, hydroxyl, straight-chain or branched $C_{1-8}$ alkoxy, suitably methoxy or ethoxy, where adjacent oxygen atoms can also be linked by $C_{1-2}$ alkylene groups, suitably by a methylene group, benzyloxy, nitro, amino, mono-$C_{1-4}$ alkylamino, di-$C_{1-4}$ alkylamino, aryl, which for its part can be unsubstituted or mono- or polysubstituted by identical or different substituents from the group of straight-chain or branched $C_{1-8}$ alkyl, $C_{3-7}$ cycloalkyl, carboxyl, straight-chain or branched $C_{1-8}$ alkoxycarbonyl, by trifluoromethyl, hydroxyl, straight-chain or branched $C_{1-8}$ alkoxy, suitably methoxy or ethoxy, benzyloxy, nitro, amino, mono-$C_{1-4}$ alkylamino, di-$C_{1-4}$ alkylamino, cyano, straight-chain or branched cyano-$C_{1-6}$ alkyl;

and their structural isomers and stereoisomers, particularly tautomers, diastereomers and enantiomers, and their pharmaceutically acceptable salts, particularly acid addition salts.

Thus, for example, the compounds of the formula (1) of the present invention which have one or more centers of chirality and which are present as racemates and can be separated by methods known per se into their optical isomers, i.e. enantiomers or diastereomers. The separation can be carried out by column separation on chiral phases or by recrystallization from an optically active solvent or using an optically active acid or base or by derivatization with an optically active reagent, such as, for example, an optically active alcohol, and subsequent removal of the radical.

Furthermore, the acridine derivatives of the formula (1) of the present invention can be converted into their salts with inorganic or organic acids, especially for pharmaceutical use, into their pharmaceutically acceptable salts. Acids which are suitable for this purpose are, for example, hydrochloric acid, hydrobromic acid, sulfuric acid, phosphoric acid, fumaric acid, succinic acid, lactic acid, citric acid, acetic acid, tartaric acid, malic acid, malonic acid, embonic acid, trifluoroacetic acid maleic acid, methonesulfuric acid, or sulfo acetic acid.

Moreover, the compounds of the formula (1) of the invention if desired can be converted if they contain a sufficiently acidic group, such as a carboxyl group, into their salts with inorganic or organic bases, especially for pharmaceutical use, into their pharmaceutically acceptable salts. Bases which are suitable for this purpose are, for example, sodium hydroxide, potassium hydroxide, calcium hydroxide, lysine, cyclohexylamine, ethanolamine, diethanolamine and triethanolamine.

According to a further embodiment, acridine derivatives of the formula (1) are provided in which R, $R_1$, $R_2$, $R_3$, X, Z, P, Q, n and m have the meanings given above and $R_4$ is phenyl which is unsubstituted or substituted by one or up to five the same or different $C_{1-6}$ alkoxy groups, in which adjacent oxygen atoms can also be linked by $C_{1-2}$ alkylene groups.

According to a further embodiment, acridine derivatives of the formula (1) are provided in which R, $R_1$, $R_2$, $R_3$, X, Z, P, Q, n and m have the meanings given above and $R_4$ is 3,5-dimethoxyphenyl.

According to a further embodiment, acridine derivatives of the formula (1) are provided in which $R_4$ has the meanings given above, R, $R_1$, $R_2$, $R_3$ each are a hydrogen atom, Z is an oxygen atom, and X is a nitrogen atom, P and Q each are two hydrogen atoms (i.e. —CH2—), m is zero and n is the integer 2.

According to a further embodiment, acridine derivatives of the formula (1) are provided in which R, $R_1$, $R_2$ and $R_3$ each are a hydrogen atom, Z is an oxygen atom, and X is a nitrogen atom, P and Q each are two hydrogen atoms (i.e. —CH2—), m is zero, n is 2, and $R_4$ is a 3,5-dimethoxyphenyl radical.

According to a yet further feature of the present invention, a process is provided for preparing acridine derivatives of formula (1) by reacting an acridine carboxylic acid of the formula (2) in which R, R1, R2, R3 have the meanings given above, Z is an oxygen or sulfur atom, and Y is a leaving group such as halogen, hydroxyl, $C_{1-6}$ alkoxy, suitably methoxy or ethoxy, —O-tosyl, —O-mesyl or imidazolyl,

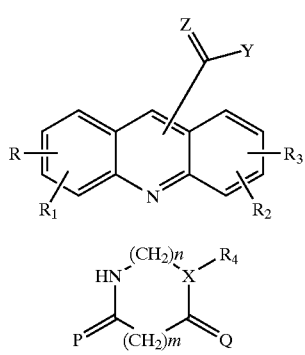

(2)

(3)

with an amine of the formula (3) in which R4, P, Q, X, m and n are as defined above, in the optional presence of diluents and auxiliaries, to form the desired acridine derivatives.

Synthesis Route

The compounds of the formula 1 can be obtained according to reaction scheme 1:

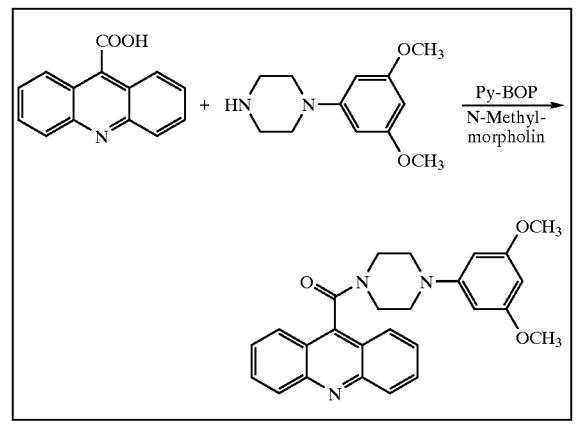

The starting materials of formulae (2) and (3) are either commercially available or can be prepared by procedures known per se. The starting materials (2) and (3) are useful intermediates for preparing the acridine derivatives of the formula (1) according to the invention.

The solvents and auxiliaries that can be optionally used, and the reaction parameters to be used, such as reaction temperature and reaction time, are known to the person skilled in the art owing to his expert knowledge.

The acridine derivatives of the formula (1) according to the present invention are suitable as medicaments, in particular as antitumor agents, for treating mammals, in particular man, but also domestic animals such as horses, cattle, dogs, cats, rabbits, sheep, poultry and the like.

According to a further feature of the present invention, a method is provided for controlling tumors in mammals, in particular man, by administering at least one acridine derivative of formula (1) to a mammal patient an amount effective for the treatment of the tumor. The therapeutically effective dose of the acridine derivative according to the invention in question which is to be administered for the treatment depends inter alia on the nature and the stage of the oncosis, the age and the sex of the patient, the type of administration and the duration of the treatment. Administration can take place orally, rectally, buccally (for example sublingually), parenterally (for example subcutaneously, intramuscularly, intradermally or intravenously), topically or transdermally.

According to a further feature of the present invention, medicaments are provided for the treatment of tumors, which comprise, as active ingredient, at least one acridine derivative of formula (1), or a pharmaceutically acceptable salt thereof, suitably together with conventional pharmaceutically acceptable auxiliaries, additives and carriers. These can be solid, semisolid, liquid or aerosol preparations. Suitable solid preparations include, for example, capsules, powders, granules, tablets. Suitable semisolid preparations include, for example, ointments, creams, gels, pastes, suspensions, oil-in-water and water-in-oil emulsions. Suitable liquid preparations include, for example, sterile aqueous preparations for parenteral administration which are isotonic with the blood of the patient.

The invention is further illustrated in more detail by the following example without being restricted to the example.

1-(3,5-Dimethoxyphenyl)-4-(9-acridinyl-carbonyl) piperazine (D-43411)

8 g (35.84 mmol) of acridine-9-carboxylic acid were charged to 300 ml of DMF with stirring. 5.79 g (57.34 mmol) of N-methylmorpholine, then a solution of 24.24 g (46.59 mmol) of Py-BOP (1-benzotriazolyltripyrrolidinophosphonium hexafluorophosphate) and 7.96 g (35.81 mmol) of 1-(3,5-dimethoxyphenyl)piperazine in 50 ml of DMF were added successively to the mixture with further stirring. The mixture was stirred at room temperature for 12 hours, the DMF was distilled off under reduced pressure and the residue was purified on a silica gel column (Kieselgel 60, from Merck AG, Darmstadt) using the mobile phase dichloromethane/methanol/ (95:5 v/v).

Yield: 12.9 (84.2% of theoretical) m.p.: 172–175° C.

1. Antiproliferative Action in Various Tumor Cell Lines

In a proliferation test, the antiproliferative activity of the substance D-43411 was examined using established tumor cell lines. The Cellular Dehydrogenation activity is determined in the test, which enables determination of the vitality of the cell and, indirectly, the cell count. The cell lines used are the human cervical carcinoma cell lines KB/HeLa (ATCC/CCL17), the murine lymphocyte leukemia L1210 (ATCC CCL-219), the human breast adenocarcinoma line MCF7/ATCC HTB22) and the ovary adenocarcinoma line SKOV-3 (ATCC HTB77). These are established cell lines which are very well characterized and were obtained from ATCC and cultured.

The results shown in Table 1 demonstrate the highly potent antiproliferative action of D-43411 in the cell lines SKOV-3, L-1210 and HeLa/KB. Due to the particularly slow growth of the MCF7 line, the effect of D-43411 in the test period of 48 h is only small (18% inhibition at 3.16 mg/ml; thus stated as >3.16).

TABLE 1

In-vitro cytotoxicity in tumor cell lines
(values determined from 5 substance concentrations)

| D number | Structure | MW | XTT - Assay IC$^{50}$ [mg/ml] | | | |
|---|---|---|---|---|---|---|
| | | | SKOV-3 | L1210 | KB/HeLa | MCF7 |
| D-43411 | | 429 | <0.0003 | <0.0003 | <0.0003 | >3.16 |

2. Method

XTT Test for Cellular Dehydrogenase Activity

The adherently growing tumor cell lines HeLa/KB, SKOV-3 and MCF7 and the L1210 leukemia line, which grows in suspension, were cultivated under standard conditions in an incubator with gas inlet at 37° C., 5% $CO_2$ and 95% atmospheric humidity. On Test Day 1, the adherent cells are detached using trypsine/EDTA and pelleted by centrifugation. The cell pellet is then resuspended in RPMI culture medium at the appropriate cell count and transferred to a 96-well microtitre plate. The plates are then overnight cultivated in the incubator with gas inlet. The test substances are made up as stock solutions in DMSO and, on Test Day 2, diluted with culture medium to the desired concentrations. The substances in the culture medium are then added to the cells and incubated in the incubator with gas inlet for 45 h. Cells which have not been treated with test substance serve as control.

1 mg/ml of XTT (sodium 3'-[1-(phenylaminocarbonyl)-3,4-tetrazolium]-bis(4-methoxy-6-nitro)benzenesulfonic acid) is dissolved for the XTT assay in RPMI-1640 medium without Phenol Red. Additionally, a 0.383 mg/ml solution is prepared of PMS (N-methyldibenzopyrazine methyl sulfate) in phosphate-buffered saline (PBS). On Test Day 4, 75 ml/well of the XTT-PMS mixture are pipetted onto the cell plates, which by now have been incubated with the test substances for 45 hours. To this end, the XTT solution is mixed with the PMS solution in a ratio of 50:1 (v/v) shortly before use. The cell plates are then incubated in the incubator with gas inlet for a further 3 hours, and the optical density ($OD_{490nm}$) is determined in a photometer.

Using the $OD_{490nm}$ obtained, the inhibition is calculated in percent relative to the control. The antiproliferative activity is estimated using regression analysis.

EXAMPLE I

Tablet containing 50 mg of active compound

Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| Total: | 215.0 mg |

Preparation

Components (1), (2) and (3) are mixed and granulated with an aqueous solution of (4). The dried granules are admixed with (5). This mixture is tabletted.

EXAMPLE II

Capsule containing 50 mg of active compound

Composition:

| | |
|---|---|
| (1) Active compound | 50.0 mg |
| (2) Maize starch, dried | 58.0 mg |
| (3) Lactose powder | 50.0 mg |
| (4) Magnesium stearate | 2.0 mg |
| Total: | 160.0 mg |

Preparation (1) is ground with (3). This ground material is added with vigorous mixing to the mixture of (2) and (4). This powder mixture is, on a capsule filling machine, filled into hard gelatine capsules size 3.

TABLE 9

New Acridinyl-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 1 | H | H | H | H | N | O | 2 | 0 | $H_2$ | $H_2$ | | 43411 | 428 |
| 2 | H | H | H | H | N | O | 2 | 0 | $H_2$ | $H_2$ | | 82266 | 394 |
| 3 | H | H | H | H | N | O | 2 | 0 | $H_2$ | $H_2$ | | 81694 | 437 |
| 4 | H | H | H | H | N | O | 2 | 0 | $H_2$ | $H_2$ | | 81745 | 396 |
| 5 | H | H | H | H | N | O | 2 | 0 | $H_2$ | $H_2$ | | 81803 | 432 |
| 6 | H | H | H | H | N | O | 2 | 0 | $H_2$ | $H_2$ | | 81804 | 384 |
| 7 | H | H | H | H | N | O | 2 | 0 | $H_2$ | $H_2$ | | 81805 | 396 |

TABLE 10

New Acridinyl-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 8 | H | H | H | H | N | O | 2 | 0 | $H_2$ | $H_2$ | | 81851 | 370 |
| 9 | H | H | H | H | N | O | 2 | 0 | $H_2$ | $H_2$ | | 81854 | 405 |
| 10 | H | H | H | H | N | O | 2 | 0 | $H_2$ | $H_2$ | | 81439 | 404 |
| 11 | H | H | H | H | CH | O | 2 | 0 | $H_2$ | $H_2$ | | 81806 | 367 |
| 12 HCl-Salz | H | H | H | H | N | O | 2 | 0 | $H_2$ | $H_2$ | | 81852 | 428 |
| 13 | H | H | H | H | N | O | 2 | 0 | $H_2$ | $H_2$ | | 82316 | 383 |
| 14 | H | H | H | H | N | O | 2 | 0 | $H_2$ | $H_2$ | | 82317 | 396 |

TABLE 11

New Acridinyl-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 15 | H | H | H | H | N | O | 2 | 0 | $H_2$ | $H_2$ | | 82318 | 398 |
| 16 | H | H | H | H | N | O | 2 | 0 | $H_2$ | $H_2$ | | 82673 | 359 |
| 17 | H | H | H | H | N | O | 2 | 0 | $H_2$ | $H_2$ | | 82747 | 400 |

We claim:

1. An acridine compound the formula

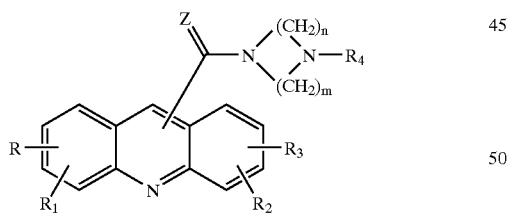

wherein

R, $R_1$, $R_2$, $R_3$ can be attached to any of the acridine carbon atoms $C_{1-9}$ and are independently of one another hydrogen, hydroxyl, a straight chain or branched chain $C_{1-8}$ alkyl, $C_{3-9}$ cycloalkyl, straight chain or branched chain $C_{1-8}$ alkylcarbonyl, straight chain or branched chain $C_{1-8}$ alkoxy, halogen, aryl-$C_{1-8}$ alkoxy, nitro, amino, mono-$C_{1-4}$ alkylamino, di-$C_{1-4}$ alkylamino, $C_{1-8}$ alkoxycarbonylamino-$C_{1-8}$ alkyl, cyano, straight chain or branched chain cyano-$C_{1-6}$ alkyl, carboxyl, $C_{1-4}$ alkoxycarbonyl, $C_{1-4}$ alkyl which is substituted by one or more fluorine atoms, carboxy-$C_{1-8}$ aryl or $C_{1-8}$ alkoxycarbonyl-$C_{1-5}$alkyl, $C_{2-6}$ alkenyl, $C_{2-6}$ alkynyl, straight chain or branched chain cyano-$C_{1-5}$ alkyl, aryl where the aryl radical can be unsubstituted or mono- or polysubstituted by the same or different substituents from the group of halogen, straight chain or branched chain $C_{1-8}$ alkyl, $C_{3-7}$ cycloalkyl, carboxyl, straight chain or branched chain $C_{1-8}$ alkoxycarbonyl, trifluoromethyl, hydroxyl, straight chain or branched chain $C_{1-8}$ alkoxy, benzyloxy, nitro, amino, mono-$C_{1-4}$ alkylamino, di-$C_{1-4}$ alkylamino, cyano, straight chain and branched chain cyano-$C_{1-4}$ alkyl, Z is oxygen or sulfur, where the radical

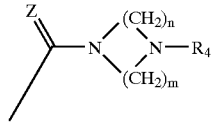

substituted onto the acridine heterocycle can be attached to any one of the $C_{1-8}$ atoms of the acridine ring skeleton, n, and m are independently of each other a cardinal number between 1 and 3, and $R_4$ is a straight chain or branched chain $C_{1-20}$ alkyl radical which can be saturated or unsaturated, with one to three double and/or triple bonds, and which can be unsubstituted or substituted at the same or different carbon atoms by one, two, or more of aryl, heteroaryl, halogen, cyano, —C=NH(NH$_2$), C$_{1-6}$ alkoxycarbonylamino, C$_{1-6}$ alkoxy, mono-C$_{1-4}$ alkylamino or di-C$_{1-4}$ alkylamino; carboxy, C$_{1-4}$ alkoxycarbonyl, a C$_{6-14}$ aryl radical, C$_{6-14}$ aryl-C$_{1-4}$ alkyl radical or a C$_{2-10}$ heteroaryl or C$_{2-10}$ heteroaryl-C$_{1-4}$ alkyl radical which contains one or more heteroatoms N, O and S, where the C$_{1-4}$ alkyl radical can be unsubstituted or mono- or polysubstituted by the same or different substituents from the group of C$_{1\,6}$ alkyl, halogen or oxo (=O) and where the C$_{6-14}$ aryl or C$_{2-10}$ heteroaryl radical can be unsubstituted or mono- or polysubstituted by the same or different substituents from the group of straight chain or branched chain C$_{1-4}$ alkyl, C$_{3-7}$ cycloalkyl, halogen, cyano, C$_{1-6}$ alkoxycarbonylamino, C$_{1-6}$ alkoxy, carboxyl, C$_{1-8}$ alkoxycarbonyl, straight chain or branched chain C$_{1-8}$ alkoxy, where adjacent oxygen atoms can also be linked by C$_{1-2}$ alkylene groups, benzyloxy, nitro, amino, mono-C$_{1-4}$ alkylamino, di-C$_{1-4}$ alkylamino, aryl which for its part can be unsubstituted or mono- or polysubstituted by the same or different substituents from the group of straight chain or branched chain C$_{1-8}$ alkyl, C$_{3-7}$ cycloalkyl, carboxyl, straight chain or branched chain C$_{1-8}$ alkoxycarbonyl, trifluoromethyl, hydroxyl, straight chain or branched chain C$_{1-8}$ alkoxy, benzyloxy, nitro, amino, mono-C$_{1-4}$ alkylamino, di-C$_{1-4}$ alkylamino, cyano, straight chain or branched chain cyano-C$_{1-6}$ alkyl;

or a pharmaceutically acceptable salt.

2. An acridine compound of claim 1, wherein R, R$_1$, R$_2$, and R$_3$ said C$_{1-8}$ alkylcarbonyl is acetyl, said aryl-C$_{1-8}$ alkoxy is benzyloxy, or phenylethoxy, said fluorine atoms are a part of a trifluoromethyl group, said C$_{2-6}$ alkenyl is allyl, said C$_{2-6}$ alkynyl is ethynyl or propargyl, said cyano-C$_{1-6}$ alkyl is cynanomethyl, said C$_{1-8}$ alkoxycarbonyl is butoxycarbonyl, and said C$_{1-8}$ alkoxy is methoxy or ethoxy, and in R$_4$ said fluorine atoms are part of trifluoromethyl, said C$_{1-8}$ alkoxy is methoxy or ethoxy, and said C$_{1-2}$ alkylene is methylene.

3. An acridine compound of claim 1, wherein R$_4$ is phenyl which is unsubstituted or substituted by one or up to five of the same or different C$_{1-6}$ alkoxy groups, wherein adjacent oxygen alkoxy can also be linked by C$_{1-2}$ alkylene groups.

4. An acridine compound of claim 1, wherein R$_4$ is 3,5-dimethyloxyphenyl.

5. A process for preparing an acridine compound of claim 1, which comprises reacting an acridine carboxylic acid of the formula

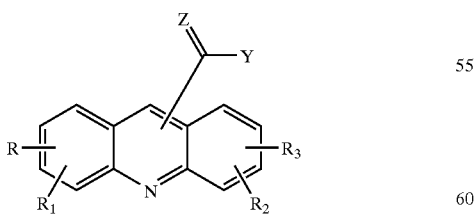

wherein R, R$_1$, R$_2$, and R$_3$, have the meanings given above, Z is an oxygen or sulfur atom, and Y is a leaving group wherein said leaving group is halogen, hydroxyl, C$_{1-6}$ alkoxy, —O-tosyl, —O-mesyl, or imidazolyl, with an amine of the formula

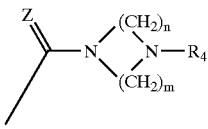

wherein Z, m, n, and R$_4$ have the same meaning as in claim 1.

6. A method of treating tumors in mammals, which comprises administering to said mammal an antitumor effective amount of at least one acridine compound of claim 1.

7. A pharmaceutical composition comprising at least one acridine compound of claim 1 and a pharmaceutically accented carrier.

8. A pharmaceutically acceptable acid addition salt of the acridine compound of claim 1, wherein formed with one of the acids hydrochloric acid, hydrobromic acid, sulfuric acid, phosphoric acid, fumaric acid, succinic acid, lactic acid, citric acid, acetic acid, tartaric acid, maleic acid, malonic acid, embonic acid, trifluoroacetic acid, malic acid, methanesulfuric acid, or sulfoacetic acid.

9. An Acridine compound of the formula according to claim 1 wherein that R, R$_1$, R$_2$, R$_3$, Z, n and m have the meanings given in claim 1 and R$_4$ is
(a) a straight-chain or branched (C$_1$–C$_{20}$)-alkyl radical which can be saturated or unsaturated, with one to three double and/or triple bonds, and which can be unsubstituted or optionally substituted on the same or different C atoms by one, two or more aryl, heteroaryl, halogen, (C$_1$–C$_6$)-alkoxy, amino, mono-(C$_1$–C$_4$) alkylamino or di-(C$_1$–C$_4$)-alkylamino;
(b) a phenyl ring or a naphthyl ring, each of which can be unsubstituted or mono- or polysubstituted by identical or different substituents from the group consisting of straight-chain or branched (C$_1$–C$_8$)-alkyl, (C$_3$–C$_7$)-cycloalkyl, halogen, cyano, (C$_1$–C$_6$)-alkoxycarbonylamino, (C$_1$–C$_6$)-alkoxy, carboxyl, (C$_1$–C$_8$)-alkoxycarbonyl, straight-chain or branched (C$_1$–C$_6$)-alkyl which is substituted by one or more fluorine atoms, hydroxyl, straight-chain or branched (C$_1$–C$_8$)-alkoxy, benzyloxy, nitro, amino, mono-(C$_1$–C$_4$)-alkylamino, di-(C$_1$–C$_4$)-alkylamino, aryl, which can be unsubstituted or mono- or polysubstituted by identical or different substituents from the group consisting of straight-chain or branched (C$_1$–C$_8$)-alkyl, (C$_3$–C$_7$)-cycloalkyl, carboxyl, straight-chain or branched (C$_1$–C$_8$)-alkoxycarbonyl, trifluoromethyl, hydroxyl, straight-chain or branched (C$_1$–C$_8$)-alkoxy, benzyloxy, nitro, amino, mono-(C$_1$–C$_4$-alkylamino, di-(C$_1$–C$_4$)-alkylamino, cyano, straight-chain or branched cyano-(C$_1$–C$_6$)-alkyl;
(c) a 2-, 4-, 5- or 6-pyrimidinyl radical or 2-, 4-, 5- or 6-pyrimidinyl -(C$_1$–C$_4$)-alkyl radical, where the (C$_1$–C$_4$)-alkyl radical can be unsubstituted or monopolysubstituted by identical or different substituents from the group consisting of (C$_1$–C$_6$)-alkyl, halogen and oxo (=O) and the 2-, 4-, 5- or 6-pyrimidinyl radical can be unsubstituted or mono- to trisubstituted by identical or different substituents from the group consisting of hydrogen, (C$_1$–C$_6$)-alkyl, halogen, nitro, amino, mono- (C$_1$–C$_6$)-alkylamino, di-(C$_1$–C$_6$)-alkylamino, hydroxyl, (C$_1$–C$_6$)-alkoxy, benzyloxy, carboxyl, (C$_1$–C$_6$-alkoxycarbonyl, ($C_1$–$C_6$)-alkoxycarbonylamino or ($C_1$–$C_6$)-alkyl which is mono- or polysubstituted by fluorine, ($C_6$–$C_{10}$)-aryl and ($C_6$–$C_{10}$)-aryl-($C_1$–$C_6$)-alkyl;

(d) a 3-, 4-, 5- or 6-pyridazinyl radical or 3-, 4-, 5-or 6-pyridazinyl -($C_1$–$C_4$)-alkyl radical, where the ($C_1$–$C_4$)-alkyl radical can be unsubstituted or mono- pr polysubstituted by identical or different substituents from the group consisting of($C_1$–$C_6$)-alkyl halogen and oxo (=O) and the 3-, 4-, 5- or 6-pyridazinyl radical can be unsubstituted or mono- to trisubstituted by identical or different substituents from the group consisting of hydrogen, ($C_1$–$C_6$)-alkyl, halogen, nitro, amino, mono-($C_1$–$C_6$)-alkylamino, di-($C_1$–$C_6$) -alkylamino, hydroxyl, ($C_1$–$C_6$)-alkoxy, benzyloxy, carboxyl, ($C_1$–$C_6$)-alkoxycarbonyl, ($C_1$–$C_6$)-alkoxycarbonylamino or ($C_1$–$C_6$) -alkyl which is mono- or polysubstituted by fluorine, ($C_6$–$C_{10}$)-aryl and ($C_6$–$C_{10}$)-aryl-($C_1$–$C_6$)-alkyl;

(e) a 2-, 3-, 5- or 6-pyrazinyl radical or 2-, 3-, 5- or 6-pyrazinyl-($C_1$–$C_4$)-alkyl radical, where the ($C_1$–$C_4$)-alkyl radical can be unsubstituted or mono- or polysubstituted by identical or different substituents from the group consisting of($C_1$–$C_6$)-alkyl, halogen and oxo (=O) and the 2-, 3-, 5- or 6-pyrazinyl radical can be unsubstituted or mono- to trisubstituted by identical or different substituents from the group consisting of hydrogen, ($C_1$–$C_6$)-alkyl, halogen, nitro, amino, mono-( $C_1$–$C_6$)-alkylamino, di-($C_1$–$C_6$) -alkylamino, hydroxyl, ($C_1$–$C_6$)-alkoxy, benzyloxy, carboxyl, ($C_1$–$C_6$)-alkoxycarbonyl, ($C_1$–$C_6$)-alkoxycarbonylamino or ($C_1$–$C_6$) -alkyl which is mono- or polysubstituted by fluorine, ($C_6$–$C_{10}$)-aryl and ($C_6$–$C_{10}$)- aryl-( $C_1$–$C_6$)-alkyl;

(f) a 3-, 4-, 5-, 6-, 7-, or 8-cinnolinyl radical or 3-, 4-, 5-, 6-, 7-, or 8-cinnolinyl-($C_1$–$C_4$)-alkyl radical, where the ($C_1$–$C_4$)-alkyl radical can be unsubstituted or mono-or polysubstituted by identical or different substituents from the group consisting of($C_1$–$C_6$-alkyl, halogen and oxo (=O) and the 3-, 4-, 5-, 6-, 7-, or 8-cinnolinyl radical can be unsubstituted or mono- to pentasubstituted by identical or different substituents from the group consisting of hydrogen, ($C_1$–$C_6$)-alkyl, halogen, nitro, amino, mono-($C_1$–$C_6$)-alkylamino, di-( $C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$) -alkoxycarbonylamino or ($C_1$–$C_6$)-alkyl which is mono- or polysubstituted by fluorine, ($C_6$–$C_{10}$)-aryl and ($C_6$–$C_{10}$)-aryl-($C_1$–$C_6$)-alkyl;

(g) a 2-, 4-, 5-, 6-, 7-, or 8-quinazolinyl radical or 2-, 4-, 5-, 6-, 7-, or 8-quinazolinyl-( $C_1$–$C_4$)-alkyl radical, where the ($C_1$–$C_4$)-alkyl radical can be unsubstituted or mono- or polysubstituted by identical or different substituents from the group consisting of hydrogen, ($C_1$–$C_6$)-alkyl, halogen and oxo (=O) and the 2-, 4-, 5-, 6-, 7-, or 8-quinazolinyl radical can be unsubstituted or mono- to pentasubstituted by identical or different substituents from the group consisting of hydrogen, ($C_1$–$C_6$)-alkyl, halogen, nitro, amino, mono-( $C_1$–$C_6$)-alkylamino, di-($C_1$–$C_6$) -alkylamino, hydroxyl, ($C_1$–$C_6$)-alkoxy, benzyloxy, carboxyl, ($C_1$–$C_6$) -alkoxycarbonyl, ($C_1$–$C_6$)-alkoxycarbonylamino or alkyl which is mono- or polysubstituted by fluorine, ($C_6$–$C_{10}$)-aryl and ($C_6$–$C_{10}$)- aryl-($C_1$–$C_6$)-alkyl;

(h) a 2-, 3-, 5-, 6-, 7-, or 8-quinoxalinyl radical, 2-, 3-, 5-, 6-, 7-, or 8-quinoxalinyl-($C_1$–$C_4$)-alkyl radical, where the ($C_1$–$C_4$-alkyl radical can be unsubstituted or mono-or polysubstituted by identical or different substituents from the group consisting of ($C_1$–$C_6$)-alkyl, halogen and oxo (=O) and the 2-, 3-, 5-, 6-, 7-, or 8-quinoxalinyl radical can be unsubstituted or mono- to pentasubstituted by identical or different substituents from the group consisting of hydrogen, ($C_1$–$C_6$)-alkyl, halogen, nitro, amino, mono-( $C_1$–$C_6$)-alkylamino, di-( $C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$) -alkoxycarbonylamino or ($C_1$–$C_6$)-alkyl which is mono- or polysubstituted by fluorine, ($C_6$–$C_{10}$) -aryl and ($C_6$–$C_{10}$)-aryl-($C_1$–$C_6$)-alkyl;

(i) a 1-, 4-, 5-, 6-, 7-, or 8-phthalazinyl radical or N, 4-, 5-, 6-, 7-, or 8-phthalazinyl-( $C_1$–$C_4$)-alkyl radical, where the ($C_1$–$C_4$)-alkyl radical can be unsubstituted or mono-or polysubstituted by identical or different substituents from the group consisting of ($C_1$–$C_6$)-alkyl, halogen and oxo (=O) and the 1-, 4-, 5-, 6-, 7-, or 8-phthalazinyl radical can be unsubstituted or mono- to pentasubstituted by identical or different substituents from the group consisting of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$) -alkoxycarbonylamino or ($C_1$–$C_6$)-alkyl which is mono- or polysubstituted by fluorine, ($C_6$–$C_{10}$) -aryl and ($C_6$–$C_{10}$)-aryl-($C_1$–$C_6$)-alkyl;

(j) a 2-, 3-, 4-, 5-, 6-, 7- or 8-quinolyl radical or 2-, 3-, 4-, 5-, 6-, 7 or 8-quinolyl-($C_1$–$C_4$-alkyl radical, where the ($C_1$–$C_4$)-alkyl radical can be unsubstituted or mono- or polysubstituted by identical or different substituents from the group consisting of ($C_1$–$C_6$)-alkyl, halogen and oxo (=O) and the 2-, 3-, 4-, 5-, 6-, 7- or 8-quinolyl radical can be unsubstituted or mono- to hexasubstituted by identical or different substituents from the group consisting of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$) -alkoxycarbonylamino or ($C_1$–$C_6$)-alkyl which is mono- or polysubstituted by fluorine, ($C_6$–$C_{10}$) -aryl and ($C_1$–$C_6$)- aryl-($C_1$–$C_6$)-alkyl;

(k) a 1-, 3-, 4-, 5-, 6-, 7- or 8-isoquinolyl radical or 1-, 3-, 4-, 5-, 6-, 7- or 8-isoquinolyl-($C_1$–$C_4$). alkyl radical, where the ($C_1$–$C_4$)-alkyl radical can be unsubstituted or mono- or polysubstituted by identical or different substituents from the group consisting of ($C_1$–$C_6$)-alkyl, halogen and oxo (=O) and the 1-, 3-, 4-, 5-, 6-, 7- or 8-isoquinolyl radical can be unsubstituted or mono- to hexasubstituted by identical or different substituents from the group consisting of hydrogen, ($C_1$–$C_6$)-alkyl, halogen, nitro, amino, mono-($C_1$–$C_6$)-alkylamino, di-($C_1$–$C_6$)-alkylamino, hydroxyl, ($C_1$–$C_6$)-alkoxy, benzyloxy, carboxyl, ($C_1$–$C_6$)-alkoxycarbonyl, ($C_1$–$C_6$) -alkoxycarbonylamino or ($C_1$–$C_6$)-alkyl which is mono- or polysubstituted by fluorine, ($C_6$–$C_{10}$)-aryl and ($C_6$–$C_{10}$)- aryl-($C_1$–$C_6$)-alkyl;

(l) a 2-, 6-, 8- or 9-[9H]-purinyl radical or 2-, 6-, 8- or 9-[9H]-purinyl-($C_1$–$C_4$)-alkyl radical, where the ($C_1$–$C_4$)-alkyl radical van be unsubstituted or mono- or polysubstituted by identical or different substituents from the group consisting of ($C_1$–$C_6$)-alkyl, halogen and oxo (=O) and the 2-, 6-, 8- or 9-[9H]-purinyl radical can be unsubstituted or mono- to trisubstituted by identical or different substituents from the group consisting of hydrogen, $(C_1-C_6)$-alkyl, halogen, intro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6)$-alkyl;

(m) a 2-, 6-, 7- or 8-[7H]-purinyl radical or 2-, 6-, 7- or 8-[7H]-purinyl-$(C_1-C_4)$-alkyl radical, where the $(C_1-C_4)$-alkyl radical can be unsubstituted or mono- or polysubstituted by identical or different substituents from the group consisting of$(C_1-C_6)$-alkyl, halogen and oxo (=O) and the 2-, 6-, 7- or 8-[7H]-purinyl radical may be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or alkyl which is mono- or polysubstituted by fluorine, $(C_6-C_{10})$-aryl and $(C_6-C_{10})$- aryl-$(C_1-C_6)$-alkyl;

(n) a 1-, 2-, 3-, 4-, 5-, 6-, 7-, 8- or 9-acridinyl radical or 1-, 2-, 3-, 4-, 5-, 6-, 7-, 8- or 9-acridinyl-$(C_1-C_4)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 1-, 2-, 3-, 4-, 5-, 6-, 7-, 8- or 9-acridinyl radical can be unsubstituted or mono- to octasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or alkyl which is mono- or polysubstituted by fluorine, $(C_6-C_{10})$-aryl and $(C_6-C_{10})$-aryl-$(C_1-C_6)$-alkyl;

(o) a 1-, 2-, 3-, 4-, 5-, 6-, 7-, 8- or 9-phenanthridinyl radical or 1-, 2-, 3-, 4-, 5-, 6-, 7-, 8- or 9-phenanthridinyl-$(C_1-C_6)$-alkyl radical, where the $(C_1-C_6)$-alkyl radical can be unsubstituted or mono- or polysubstituted by identical or different substituents from the group consisting of hydrogen, $(C_1-C_6)$-alkyl, halogen and oxo (=O) and the 1-, 2-, 3-, 4-, 5-, 6-, 7-, 8- or 9-phenanthridinyl radical can be unsubstituted or mono- to octasubstituted by identical or different substituents from the group consisting of $(C_1-C_6)$-alkyl, halogen, nitro, amino, mono-$(C_1-C_6)$-alkylamino, di-$(C_1-C_6)$ -alkylamino, hydroxyl, $(C_1-C_6)$-alkoxy, $(C_6-C_{10})$-aryl-$(C_1-C_6)$ -alkoxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, $(C_6-C_{10})$ -aryl and $(C_6-C_{10})$-aryl-$(C_1-C_6)$-alkyl;

(p) a 2-, 3-, 4-, 5- or 6-pyridyl radical where the 2-, 3-, 4-, 5- or 6-pyridinyl radical can be unsubstituted or mono- to tetrasubstituted by identical or different substituents from the group consisting of hydrogen, $(C_1-C_6$-alkyl, halogen, nitro, amino, mono-$(C_1-C_6)$ -alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$ -alkoxycarbonylamino or $(C_1-C_6)$-alkyl which is mono- or polysubstituted by fluorine, $(C_6-C_{10})$-aryl and $(C_6-C_{10})$-aryl-$(C_1-C_6)$-alkyl;

(q) a 2-, 3-, 4-, 5- or 6-pyridyl-$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 2-, 3-, 4-, 5- or 6-pyridinyl radical can be unsubstituted or mono- to tetrasubstituted by identical or different substituents from the group consisting of hydrogen, $(C_1-C_6)$-alkyl, halogen, nitro, amino, mono-$(C_1-C_6)$ -alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$ -alkoxycarbonylamino or $(C_1-C_6)$-alkyl which is mono- or polysubstituted by fluorine, $(C_6-C_{10})$ -aryl and $(C_6-C_{10})$-aryl-$(C_1-C_6)$-alkyl;

(r) a 2-, 3-, 4- or 5-thienyl radical or 2-, 3-, 4- or 5-thienyl-$(C_1-C_6)$ -alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 2-, 3-, 4- or 5-thienyl radical can be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$ -alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$aryl and $(C_6-C_{10})$-aryl-$(C_1-C_6)$-alkyl;

(s) a 2-, 4-, or 5-thiazolyl radical or 2-, 4-, or 5-thiazolyl-$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 2-, 4-, or 5-thiazolyl radical can be unsubstituted or mono- or disubstituted by identical or different substituents from the group consisting of hydrogen, $(C_1-C_6)$-alkyl, halogen, intro, amino, mono-$(C_1-C_6)$-alkylamino, di-$(C_1-C_6$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6$-alkyl;

(t) a 3-, 4-, or 5-isothiazolyl radical or 3-, 4-, or 5-isothiazolyl-$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 3-, 4-, or 5-isothiazolyl radical can be unsubstituted or mono- or disubstituted by identical or different substituents from the group consisting of hydrogen, $(C_1-C_6)$-alkyl, halogen, nitro, amino, mono-$(C_1-C_6)$-alkylamino, di-$(C_1-C_6)$ -alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_1-C_6)$aryl and $(C_6-C_{10})$-aryl-$(C_1-C_6)$-alkyl;

(u) a 2-, 4-, 5-, 6-, or 7-benzothiazolyl radical or 2-, 4-, 5-, 6-, or 7-benzothiazolyl-$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 2-, 4-, 5-, 6-, or 7-benzothiazolyl radical can be unsubstituted or mono- to tetrasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, $(C_6-C_{10})$-aryl and $(C_6-C_{10})$-aryl-$(C_1-C_6)$-alkyl;

(v) a 1-, 2-, 4-, or 5-imidazolyl radical or 1-, 2-, 4-, or 5-imidazolyl -$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 1-, 2-, 4-, or 5-imidazolyl radical can be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$-alkyl which is mono- or polysubstituted by fluorine, $(C_6-C_{10})$-aryl and $(C_6-C_{10})$-aryl-$(C_1-C_6)$-alkyl;

(w) a 1-, 3-, 4-, or 5-pyrazolyl radical or 1-, 3-, 4- or 5-pyrazolyl-$(C_1-C_6)$-alkyl radical, where the $(C_1-C_6)$-alkyl radical can be unsubstituted or mono- or polysubstituted by identical or different substituents from the group consisting of$(C_1-C_6)$-alkyl, halogen and oxo (=O) and the 1-, 3-, 4- or 5-pyrazolyl radical can be unsubstituted or mono- to trisubstituted by identical or different substituents from the group consisting of hydrogen, $(C_1-C_6)$-alkyl, halogen, nitro, amino, mono-$(C_1-C_6)$-alkylamino, di-$(C_1-C_6)$ -alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6)$-alkyl;

(x) a 1-, 2-, 3-, 4-, or 5-pyrrolyl radical or 1-, 2-, 3-, 4-, or 5-pyrrolyl -$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 1-, 2-, 3-, 4- or 5-pyrrolyl radical can be unsubstituted or mono- to tetrasubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6)$-alkyl;

(y) a 1-, 3-, or 5-[1.2.4]-triazolyl radical or 1-, 3-, or 5-[1.2.4]-triazolyl-$(C_1-C_6)$alkyl radical, where the $(C_1-C_6)$-alkyl radical can be unsubstituted or mono- or polysubstituted by identical or different substituents from the group consisting of hydrogen, $(C_1-C_6)$-alkyl, halogen and oxo (=O) and the 1-, 3-, or 5-[1.2.4]-triazolyl radical can be unsubstituted or mono- or disubstituted by identical or different substituents from the group consisting of$(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6)$-alkyl;

(z) a 1-, 4-, or 5-[1.2.3]-triazolyl radical or 1-, 4-, or 5-[1.2.3]-triazolyl-$(C_1-C_6)$-alkyl radical, where the $(C_1-C_6)$-alkyl radical can be unsubstituted or mono- or polysubstituted by identical or different substituents from the group consisting of$(C_1-C_6)$-alkyl, halogen and oxo (=O) and the 1-, 4-, or 5-[1.2.3]-triazolyl radical can be unsubstituted or mono- or disubstituted by identical or different substituents from the group consisting of hydrogen, $(C_1-C_6)$-alkyl, halogen, alto, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6)$-alkyl;

(aa) a 1- or 5-[1H]-tetrazolyl radical or 1- or 5-[1H]-tetrazolyl-$(C_1-C_6)$-alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 1-, or 5-[1H]-tetrazolyl radical can be unsubstituted or substituted by hydrogen, $(C_1-C_4$-alkyl, halogen, nitro, amino, mono-$(C_1-C_6)$-alkylamino, di-$(C_1-C_6)$ -alkylamino, hydroxyl, $(C_1-C_6)$-alkoxy, benzyloxy, carboxyl, $(C_1-C_6)$-alkoxycarbonyl, $(C_1-C_6)$-alkoxycarbonylamino or $(C_1-C_6)$ -alkyl which is mono- or polysubstituted by fluorine, $(C_6-C_{10})$-aryl and $(C_6-C_{10})$-aryl-$(C_1-C_6)$-alkyl;

(ab) a 2- or 5-[2H]-tetrazolyl radical or 2- or 5-[2H]-tetrazolyl-$(C_1-C_6)$ -alkyl radical, where the $(C_1-C_6)$-alkyl radical can be unsubstituted or mono- or polysubstituted by identical or different substituents from the group consisting of $(C_1-C_6)$-alkyl, halogen and oxo (=O) and the 2- or 5-[2H]-tetrazolyl radical can be unsubstituted or substituted by hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$ -alkoxycarbonyl, $(C_1-C_6)$-alkoxycarbonylamino or $(C_1-C_6)$-alkyl which is mono- or polysubstituted by fluorine, preferably $(C_6-C_{10})$-aryl and $(C_6-C_{10})$-aryl-$(C_1-C_6)$-alkyl;

(ac) a 2-, 4-, or 6-[1.3.5]-triazinyl radical or 2-, 4-, or 6-[1.3.5]-triazinyl-$(C_1-C_6)$-alkyl radical, where the $(C_1-C_6)$-alkyl radical can be unsubstituted or mono- or polysubstituted by identical or different substituents from the group consisting of hydrogen, $(C_1-C_6)$-alkyl halogen and oxo (=O) and the 2-, 4-, or 6-[1.3.5]-triazinyl radical can be unsubstituted or mono- or disubstituted by identical or different substituents from the group consisting of hydrogen, $(C_1-C_6)$-alkyl, halogen, nitro, amino, mono-$(C_1-C_6)$-alkylamino, di-$(C_1-C_6)$-alkylamino, hydroxyl, $(C_1-C_6)$-alkoxy, benzyloxy, carboxyl, $(C_1-C_6)$-alkoxycarbonyl, $(C_1-C_6)$ - alkoxycarbonylamino or $(C_1-C_6)$-alkyl which is mono- or polysubstituted by fluorine, $(C_6–C_{10})$-aryl and $(C_6–C_{10})$-aryl-$(C_1–C_6)$-alkyl;

(ad) a 2-, 4-, or 5-oxazolyl radical or 2-, 4-, or 5-oxazolyl-$(C_1–C_6)$-alkyl radical, where the $(C_1–C_6)$-alkyl radical can be unsubstituted or mono- or polysubstituted by identical or different substituents from the group consisting of $(C_1–C_6)$-alkyl, halogen and oxo (=O) and the 2-, 4-, or 5-oxazolyl radical can be unsubstituted or mono- or disubstituted by identical or different substituents from the group consisting of hydrogen, $(C_1–C_6)$-alkyl, halogen, nitro, amino, mono-$(C_1–C_6)$-alkylamino, di-$(C_1–C_6)$-alkylamino, hydroxyl, $(C_1–C_6)$-alkoxy, benzyloxy, carboxyl, $(C_1–C_6)$-alkoxycarbonyl, $(C_1–C_6)$-alkoxycarbonylamino or $(C_1–C_6)$-alkyl which is mono- or polysubstituted by fluorine, $(C_6–C_{10})$-aryl and $(C_6–C_{10})$-aryl-$(C_1–C_6)$-alkyl;

(ae) a 3-, 4-, or 5-isoxazolyl radical or 3-, 4-, or 5-isoxazolyl$(C_1–C_6)$-alkyl radical, where the $(C_1–C_6)$-alkyl radical can be unsubstituted or mono- or polysubstituted by identical or different substituents from the group consisting of $(C_1–C_6)$-alkyl, halogen and oxo (=O) and the 3-, 4-, or 5-isoxazolyl radical can be unsubstituted or mono- or disubstituted by identical or different substituents from the group consisting of hydrogen, $(C_1–C_6)$-alkyl, halogen, nitro, amino, mono-$(C_1–C_6)$-alkylamino, di-$(C_1–C_6)$-alkylamino, hydroxyl, $(C_1–C_6)$-alkoxy, benzyloxy, carboxyl, $(C_1–C_6)$-alkoxycarbonyl, $(C_1–C_6)$-alkoxycarbonylamino or $(C_1–C_6)$-alkyl which is mono- or polysubstituted by fluorine, $(C_6–C_{10})$-aryl and $(C_6–C_{10})$-aryl-$(C_1–C_6)$-alkyl;

(af) a 1-, 2-, 3-, 4-, 5-, 6- or 7-indolyl radical or 1-, 2-, 3-, 4-, 5-, 6- or 7-indolyl-$(C_1–C_6)$-alkyl radical, where the $(C_1–C_6)$-alkyl radical can be unsubstituted or mono- or polysubstituted by identical or different substituents from the group consisting of $(C_1–C_6)$-alkyl, halogen and oxo (=O) and the 1-, 2-, 3-, 4-, 5-, 6- or 7-indolyl radical can be unsubstituted or mono- to hexasubstituted by identical or different substituents from the group consisting of hydrogen, $(C_1–C_6)$-alkyl, halogen, intro, amino, mono-$(C_1–C_6)$-alkylamino, di-$(C_1–C_6)$-alkylamino, hydroxyl, $(C_1–C_6)$-alkoxy, benzyloxy, carboxyl, $(C_1–C_6)$-alkoxycarbonyl, $(C_1–C_6)$-alkoxycarbonylamino or $(C_1–C_6)$-alkyl which is mono- or polysubstituted by fluorine, $(C_6–C_{10})$-aryl and $(C_6–C_{10})$-aryl-$(C_1–C_6)$-alkyl.

10. An Acridine compound as claimed in claim 9, wherein said (b) is a phenyl ring or a naphthyl ring, each of which can be unsubstituted or mono- or polysubstituted by identical or different substituents from the group consisting of straight-chain or branched $(C_1–C_8)$-alkyl, $(C_3–C_7)$-cycloalkyl, halogen, cyano, $(C_1–C_6)$-alkoxycarbonylamino, $(C_1–C_6)$-alkoxy, carboxyl, $(C_1–C_8)$-alkoxycarbonyl, straight-chain or branched $(C_1–C_6)$-alkyl which is substituted by one or more fluorine atoms, hydroxyl, straight-chain or branched $(C_1–C_8)$-alkoxy, benzyloxy, nitro, amino, mono- $(C_1–C_4$-alkylamino, di-$(C_1–C_4)$-alkylamino, aryl, which can be unsubstituted or mono- or polysubstituted by identical or different substituents from the group consisting of straight-chain or branched $(C_1–C_8)$-alkyl, $(C_3–C_7)$-cycloalkyl, carboxyl, straight-chain or branched $(C_1–C_8)$-alkoxycarbonyl, trifluoromethyl, hydroxyl, methoxy, ethoxy, benzyloxy, nitro, amino, mono-$(C_1–C_4$-alkylamino, di-$(C_1–C_4)$-alkylamino, cyano, straight-chain or branched cyano-$(C_1–C_6)$-alkyl.

\* \* \* \* \*

UNITED STATES PATENT AND TRADEMARK OFFICE
CERTIFICATE OF CORRECTION

PATENT NO.    : 6,706,722 B2
DATED         : March 16, 2004
INVENTOR(S)   : Emig et al.

It is certified that error appears in the above-identified patent and that said Letters Patent is hereby corrected as shown below:

Column 7,
Line 58, "$C_{3-9}$" should read -- $C_{3-7}$ --
Line 64, "$C_{1-4}$" should read -- $C_{1-8}$ --

Column 8,
Line 49, "cyano-$C_{1-4}$" should read -- cyano-$C_{1-6}$ --

Column 9,
Line 10, "$C_{16}$" should read -- $C_{1-6}$ --

Column 10,
Line 24, "Acridine" should read -- acridine --

Column 11,
Line 20, "6-pyrazinyl-($C_1$-$C_4$-alkyl" should read -- 6-pyrazinyl-($C_1$-$C_4$)-alkyl --
Lines 20-21, "($C_1$-$C_4$-alkyl" should read -- ($C_1$-$C_4$)-alkyl --

Column 12,
Line 1, "($C_1$-$C_4$-alkyl" should read -- ($C_1$-$C_4$)-alkyl --
Line 15, "N," should read -- 1-, --
Line 65, "van" should read -- can --

Column 15,
Line 44, "($C_6$-$C_{10}$-aryl" should read -- ($C_6$-$C_{10}$)-aryl --

Column 16,
Line 33, "($C_1$-$C_4$-aryl" should read -- ($C_1$-$C_6$)-alkyl --

UNITED STATES PATENT AND TRADEMARK OFFICE
CERTIFICATE OF CORRECTION

PATENT NO. : 6,706,722 B2
DATED : March 16, 2004
INVENTOR(S) : Emig et al.

It is certified that error appears in the above-identified patent and that said Letters Patent is hereby corrected as shown below:

Column 18,
Line 13, "Acridine" should read -- acridine --

Signed and Sealed this

Twenty-seventh Day of July, 2004

JON W. DUDAS
*Acting Director of the United States Patent and Trademark Office*